United States Patent
Schröder et al.

(10) Patent No.: US 10,865,173 B2
(45) Date of Patent: Dec. 15, 2020

(54) ORGANIC COMPOUNDS

(71) Applicant: Givaudan SA, Vernier (CH)

(72) Inventors: Fridtjof Schröder, Hettlingen (CH); Nicole Pfeiffer, Fahrweid (CH)

(73) Assignee: GIVAUDAN S.A., Vernier (CH)

(*) Notice: Subject to any disclaimer, the term of this patent is extended or adjusted under 35 U.S.C. 154(b) by 0 days.

(21) Appl. No.: 16/765,235

(22) PCT Filed: Dec. 3, 2018

(86) PCT No.: PCT/EP2018/083322
§ 371 (c)(1),
(2) Date: May 19, 2020

(87) PCT Pub. No.: WO2019/110493
PCT Pub. Date: Jun. 13, 2019

(65) Prior Publication Data
US 2020/0283363 A1 Sep. 10, 2020

(30) Foreign Application Priority Data
Dec. 5, 2017 (GB) .................................. 1720211.0

(51) Int. Cl.
*C07C 45/34* (2006.01)
*B01J 31/00* (2006.01)
*B01J 31/18* (2006.01)
*B01J 35/00* (2006.01)

(52) U.S. Cl.
CPC ........... *C07C 45/34* (2013.01); *B01J 31/1815* (2013.01); *B01J 35/004* (2013.01); *B01J 2231/005* (2013.01); *B01J 2231/70* (2013.01); *B01J 2531/842* (2013.01)

(58) Field of Classification Search
CPC ...... C07C 45/34; B01J 31/1815; B01J 35/004
See application file for complete search history.

(56) References Cited

FOREIGN PATENT DOCUMENTS

| DE | 4101334 A1 | 8/1991 |
|---|---|---|
| EP | 2402301 A1 | 1/2012 |
| EP | 3255151 A2 | 12/2017 |
| FR | 2657606 A1 | 1/1991 |
| WO | 2011106166 A1 | 9/2011 |
| WO | 2011141855 A1 | 11/2011 |
| WO | 2012001018 A1 | 1/2012 |

OTHER PUBLICATIONS

Evan J. Horn, et al., Scalable and sustainable electrochemical allylic C—H oxidation, Nature, 2016, pp. 77-81, vol. 533, Issue 7601, Nature Publishing Group.
Masakazu Ishihara, et al., Guaiane Sesquiterpenes From Agarwood, Phytochemistry, 1991, pp. 3343-3347, vol. 30, Issue 10, Great Britain.
Akira Nakanishi, et al., Identification of Rotundone as a Potent Odor-Active Compound of Several Kinds of Fruits, Journal of Agricultural and Food Chemistry, May 18, 2017, pp. 4464-4471, vol. 65, American Chemical Society Publications.
An-Cheng Huang, et al., Production of the Pepper Aroma Compound, (-)-Rotundone, by Aerial Oxidation of alpha-Guaiene, Journal of Agricultural and Food Chemistry, Oct. 11, 2014, pp. 10809-10815, vol. 62, American Chemical Society Publications.
Kim Alfonsi, et al., Green chemistry tools to influence a medicinal chemistry and research chemistry based organisation, Green Chemistry, 2008, pp. 31-36, vol. 10, The Royal Society of Chemistry.
Yukie Kumeta, et al., Characterization of alpha-Guaiene Synthases from Cultured Cells of Aquilaria, Responsible for the Formation of the Sesquiterpenes in Agarwood, Plant Physiology, Dec. 2010, pp. 1998-2007, vol. 154, American Society of Plant Biologists.
An-Cheng Huang, et al., Comparison of the Formation of Peppery and Woody Sesquiterpenes Derived from alpha-Guaiene and alpha-Bulnesene under Aerial Oxidative Conditions, Journal of Agricultural and Food Chemistry, Jan. 28, 2015, pp. 1932-1938, vol. 63, American Chemical Society Publications.
International Search Report for corresponding International Application PCT/EP2018/083322.
Written Opinion of the International Searching Authority for corresponding International Application PCT/EP2018/083322.
Great Britain Search Report for corresponding application GB 1720211.0.

*Primary Examiner* — Sikarl A Witherspoon
(74) *Attorney, Agent, or Firm* — Curatolo Sidoti Co., LPA; Salvatore A. Sidoti; Floyd Trillis, III

(57) ABSTRACT

An allylic oxidation process includes forming a mixture containing α-Guaiene and an iron (III)-X porphyrin complex catalyst in a sustainable solvent, introducing molecular oxygen into the mixture, and effecting allylic oxidation to produce an α,ß-unsaturated ketone, Rotundone.

23 Claims, No Drawings

ORGANIC COMPOUNDS

CROSS REFERENCE TO RELATED APPLICATIONS

This application is a national stage application of International Application No. PCT/EP2018/083322, filed 3 Dec. 2018, which claims priority from Great Britain Patent Application No. 1720211.0, filed 5 Dec. 2017, both of which applications are incorporated herein by reference in their entireties.

The present invention is directed to a process of preparing the α,β-unsaturated ketone Rotundone 2 by allylic oxidation of α-Guaiene 1 using catalytic amounts of iron(III)porphyrin complexes in the presence of molecular oxygen and in a sustainable solvent.

There is a need for a simple, sustainable synthesis route to Rotundone ((3S,5R,8S)-5-Isopropenyl-3,8-dimethyl-3,4,5,6,7,8-hexahydro-1(2H)-azulenone) from α-Guaiene (1,4-dimethyl-7-propan-2-ylidene-2,3,4,5,6,8-hexahydro-1H-azulene) with a competitive selectivity and yield.

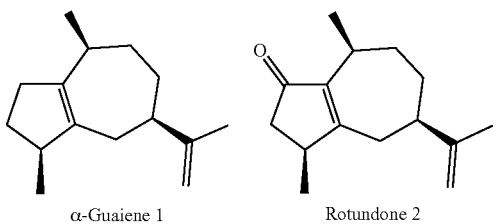

α-Guaiene 1    Rotundone 2

Unsaturated terpenes such as α-Guaiene are important substrates in the flavor and fragrance industry, giving after allylic oxidation, valuable flavor and fragrance ingredients such as Rotundone. Oxidative transformations of this substrate is especially challenging because the substrate has multiple sites which are sensitive to oxidation and can give various oxidation products arising from competing epoxidation, ene-oxidation or unselective allylic oxidation side reactions.

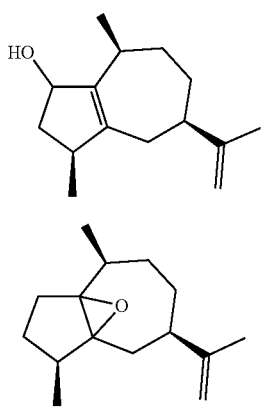

3

4

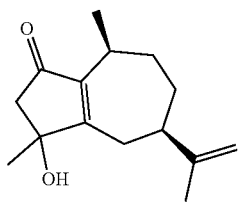

6

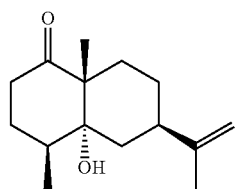

7

Potential side products include Rotundol 3, epoxy-Guaiene 4, hydroxy-Rotundone 6, and Corymbolon 7.

The method must provide a high enough selectivity and yield of Rotundone that any byproducts, which have their own odor, do not adversely affect the Rotundone odor profile if the Rotundone is used in the reaction product mixture rather than being isolated. The method should also utilize any source of α-Guaiene as the allylic substrate, an inexpensive, non-toxic catalyst, and sustainable solvent(s), as the Rotundone is intended for use in fragrances.

The isolation and oxidation of Guaiane sesquiterpenes from Agarwood was reported by Ishihara et al., *Phytochemistry* 30, 3343 (1991). A crude mixture of isolated Guaianes was subjected to oxidation in a stirred suspension of pyridinium chlorochromate and Celite in dichloromethane to yield Rotundone.

The synthesis of Rotundone was reported by Nakanishi et al., *Journal of Agricultural and Food Chemistry* 65, 4464 (2017) from (−)-guaiol by the complex process of acetylation, allylic oxidation using a combination cobalt(II) 2-ethylhexanoate, cobalt(II) acetylacetonate and cobalt(II) naphthenate catalyst and 4-methyl-2-pentanone, followed by pyrolytic elimination of acetic acid.

Taylor et al, reported in *Journal of Agricultural and Food Chemistry*, 62, 10809, (2014) the oxidation of pure α-Guaiene by bubbling oxygen through a solution of α-Guaiene in dichloromethane over a number of weeks, to produce Rotundone, the α-trans and β-cis monoepoxides of guaiene, its di-ketone, and numerous minor oxidation products incorporating one or two oxygen atoms. Similar results were obtained using other organic solvents such as ether, chloroform and acetonitrile.

The oxidation of natural products in the guaiane family by electrochemical allylic oxidation was reported by Horn and Rosen et al. in a letter to *Nature*, Vol. 533, 77 (5 May 2016) using co-oxidants tetrachloro-N-hydroxyphthalimide, pyridine, butyric acid and LiClO$_4$ in various technical grade solvents, such as acetone.

WO2011/106166 relates to allylic oxidation catalysts. An exemplary method comprises the step of catalyzing oxidation of an allylic compound using an allylic oxidation catalyst comprising palladium, gold, and titanium. Example 4 disclosed the oxidation of guaiene to form rotundone using the catalyst (2.5% Au+2.5% Pd/TiO$_2$) in an autoclave charged with oxygen at 30 bar. No yield results were reported.

There remains a need for an efficient allylic oxidation method to form the α,β-unsaturated ketone, Rotundone, in the presence of oxygen using inexpensive and nontoxic catalysts in sustainable solvents. Solvents previously used in allylic oxidation processes discussed above, such as benzene, chloroform, dichloromethane, and ether, are considered to be undesirable as pointed out by Dunn and Perry et al. *Green Chemistry* 10, 31-36 (2008) for example. Other solvents, which are not considered sustainable, include carbon tetrachloride, dimethyl formamide and dimethyl acetate, among others.

Provided is an allylic oxidation process comprising forming a mixture containing α-Guaiene and an iron(III)-X porphyrin complex catalyst in a sustainable solvent, introducing molecular oxygen into the mixture, and effecting allylic oxidation to produce an α,β-unsaturated ketone, Rotundone. X is selected from Cl, Br, I, mesylates, triflates, and carboxylates, preferably Cl, Br and I, further preferably Cl.

In one particular embodiment there is provided an allylic oxidation process as herein described, characterized in that Rotundone is produced as main product. By "main product" we mean in the context of this invention that oxidative product obtained by oxidation of α-Guaiene which is most present. This can be easily measured, e.g. by gas chromatography (GC).

In a further embodiment there is provided an allylic oxidation process as herein described, characterized in that Rotundone is produced with a GC-purity of 10% or higher (e.g. 13, 15, 20, 22, 23, 24, 25, 26, 27, 28, 29, 30) measured in % relative peak area based on the oxidative products obtained by the allylic oxidation. The GC method used for the calculation of the GC-purity is described herein below (see non polar GC).

In certain embodiments of the subject process, the catalyst is an iron (III) porphyrin complex of formula (I)

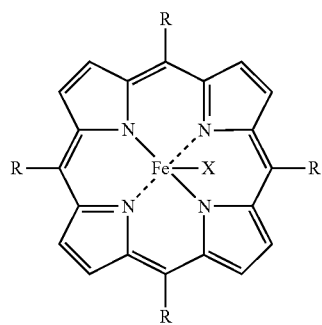

(I)

wherein
X is selected from Cl, Br and I; and
R is selected from phenyl, pentafluorophenyl, p-methoxyphenyl, dichlorophenyl, benzenesulfonate, bromophenyl, chlorophenyl, and methylphenyl.

In certain embodiments of the subject process, the catalyst is an iron (III) porphyrin complex catalyst, having a chloride counter-ion. In preferred embodiments, the porphyrin complex is a complex of formula (I) wherein R is selected from phenyl, tetraphenyl, and p-methoxyphenyl. In a particularly preferred embodiment, the catalyst is chloro(tetraphenylporphyrinato)iron(III), i.e., X is Cl and R is phenyl.

In certain embodiments, the concentration of catalyst may be in the range of 0.01 to 10 mol %, preferably 0.5 to 2 mol %, e.g. 1-1.5 mol % which includes 1.1 mol %, based on the number of mols of α-Guaiene.

In the subject process, the mixture may additionally contain a base coordination compound, for example, an amine, such as triethylamine or an inorganic base, such as $K_2CO_3$. The base coordination compound is preferably an N-heterocycle (an N-containing heterocycle), such as pyridine, imidazole or N-methylimidazole, further preferably imidazole.

The sustainable solvent used in the subject process may be selected from the group consisting of water, acetone, ethanol, 2-propanol, ethyl acetate, isopropyl acetate, methanol, methyl ethyl ketone, 1-butanol, t-butanol and mixtures thereof, preferably an ethanol/water mixture. The suitability of aqueous ethanol as a solvent for this reaction is surprising, because ethanol as such may be oxidized, and water is not the solvent which one would typically use in organic chemistry reactions.

Additionally or alternatively, the sustainable solvent used in the subject process may be selected from the group consisting of cyclohexane, heptane, toluene, methylcyclohexane, methyl t-butyl ether, isooctane, acetonitrile, xylenes, dimethyl sulfoxide, acetic acid, ethylene glycol and mixtures thereof.

The subject process preferably includes stirring the mixture by any suitable means known in the art. In a preferred embodiment, the reaction may proceed from −10° C. (freezing point of the water/ethanol reaction mixture) to 78° C. (boiling point of the water/ethanol reaction mixture). A preferred range is about 35 to about 55° C.

In the subject process, the step of introducing molecular oxygen into the mixture comprises bubbling oxygen gas into the mixture. In certain embodiments, introducing molecular oxygen into the mixture comprises bubbling air into the mixture. Alternatively, molecular oxygen may be introduced into the mixture by reacting in an oxygen atmosphere with strong stirring. Molecular oxygen may also be introduced into the mixture by processing the reaction in a flow reactor.

Although not required, the subject process may include exposing the mixture to electromagnetic radiation, preferably UV and visible light radiation. The wavelength range of the light used to expose the mixture may be in the range of about 200 nm to about 800 nm. Alternatively, the process may be carried out in the dark, or under ambient light conditions.

In the subject process, produced α,β-unsaturated ketone, Rotundone, obtained in a mixture may be further purified by means known to the person skilled in the art. For example the crude mixture may be purified by bulb-to-bulb distillation, e.g, at about 150-230° C. at 0.04-0.1 mbar, optionally followed by flash chromatography.

Guaienes are natural chemical compounds that have been isolated from a variety of plant sources. The guaienes are sesquiterpenes with the molecular formula $C_{15}H_{24}$. α-Guaiene was first isolated from guaiac wood oil. As another natural source of α-Guaiene one may mention patchouli oil or light fraction thereof. α-Guaiene obtained by biotechnological production, e.g. by fermentation of sugars, may also be used. The biotechnological production is described for example in WO 2011/141855 A1 and in Plant Physiol 2010, 154, 1998-2007. Mixtures comprising α-Guaiene used for the process described herein, preferably contain at least 15 weight % (which includes 20 wt %, 30 wt %, 40 wt %, 50 wt %, 60 wt %, 70 wt %, 75 wt %, 80 wt %, 85 wt %, 90 wt % or more) α-Guaiene.

The disclosure is now further described with reference to the following non-limiting examples. These examples are for the purpose of illustration only and it is understood that variations and modifications can be made by one skilled in the art.

Analytical Procedures Employed

Polar GCMS: 35° C./2 min, 10° C./min to 50° C., 2.5° C./min to 240° C., 240° C./5 min. Thermo Scientific TSQ8000evo+Trace 1310 system. Polar column: Varian VF-WAX (polar, PEG phase). Column dimensions: 30 m length, 0.25 mm ID, 0.25 μm film thickness. Injector: splitless. Flow: 1.2 ml/min. Carrier gas: Helium. Injection volume: 1 μl. Injector temperature: 230° C. Transfer line: 250° C. MS-quadrupol: 160° C. MS-source: 230° C. Ionization mode: Electron Impact (EI) at 70 eV. By this method GC-conversion and product distribution was measured and relative peak areas of the main components 1-7 are given in %.

Nonpolar GC: 100° C./2 min, 15° C./min to 240° C., 240° C./5 min. Thermo Focus GC. Nonpolar column: Agilent Technologies J&W Scientific DB-5 (nonpolar, 5% Phenyl-methylpolysiloxane). Column dimensions: 30 m length, 0.32 mm ID, 0.25 μm film thickness. Injector: Split. Injector temperature: 240° C. Detector: FID. Detector temperature: 270° C. Injection volume: 1 μl. Carrier gas: Helium. Split ratio: 1/42.3. Pressure: 70 kPa. Integrator: Hewlett Packard. By this method the GC-purity of Rotundone 2 after distillation was measured in % rpa (relative peak area).

α-Guaiene 91% was isolated from Guaiac wood oil by a modified literature procedure (D. K. Taylor et al. Agric & Food Chem. 63, 1932, 2015). The purity of α-Guaiene 91% was determined by $^{1}$H-NMR with the internal standard anisaldehyde. NMR spectra were measured in CDCl$_3$ at 400 MHz.

(4S,7R)-4-methyl-7-(prop-1-en-2-yl)-3,4,5,6,7,8-hexahydroazulen-1(2H)-one (compound 5; ketone 5) was identified in all mixtures, which have been obtained in the subject process as herein described. Its odor was described being woody, cedary, dry, isoraldeine-guaiac, smokey, fruity, spicy.

5

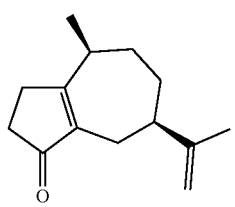

Analytical data of ketone 5: $^{1}$H-NMR (benzene-D$_6$, 400 MHz): 4.85-4.9 (2 s, 2H), 3.1-3.14 (2H), 2.5-1.4 (10H), 1.75 (s, 3H), 0.9 (d, 3H) ppm. $^{13}$C-NMR (benzene-D$_6$, 400 MHz): 206.5 (s), 176.6 (s), 150.3 (s), 139.0 (s), 108.9 (t), 45.2 (d), 36.4 (d), 33.8 (t), 32.1 (t), 30.9 (t), 29.5 (t), 28.1 (t), 20.4 (q), 16.5 (q) ppm. $^{13}$C-NMR (CDCl$_3$, 400 MHz): 209.3 (s), 179.9 (s), 150.6 (s), 139.2 (s), 108.9 (t), 45.3 (d), 36.85 (d), 34.3 (t), 32.3 (t), 31.0 (t), 30.15 (t), 27.2 (t), 20.6 (q), 17.0 (q) ppm. The structure was confirmed by the following NMR-analytical methods: COSYDQF, HSQC, HMBC and NOESY. IR (cm$^{-1}$): 2661 (w), 2922 (m), 2854 (w), 1697 (s), 1642 (m), 1452 (w), 1438 (w), 1375 (w), 1304 (w), 1286 (w), 1260 (w), 1236 (w), 1173 (w), 1154 (w), 1071 (w), 1042 (w), 1023 (w), 992 (w), 886 (m), 532 (w). GCMS (EI, m/z): 204 (2%, [M]$^{+}$), 189 (11%, [M−15]$^{+}$), 161 (12%), 148 (51%), 147 (48%), 134 (10%), 133 (100%), 121 (18%), 119 (28%), 107 (19%), 106 (11%), 105 (43%), 93 (25%), 91 (18%), 91 (39%), 81 (34%), 81 (17%), 79 (27%), 77 (22%). $[\alpha]_D^{22}$=−11.4 (c 0.35, CHCl$_3$). HRMS (ESI): Calcd for C$_{14}$H$_{21}$O [M+H]$^{+}$: 205.1587; Found: 205.1586.

EXAMPLE 1. PREPARATION OF ROTUNDONE 2 FROM α-GUAIENE 1 UNDER FE(III)-CATALYSIS AND LIGHT IRRADIATION (PHOTOCATALYTIC)

Chloro(tetraphenylporphyrinato)iron(III) (34 mg, 0.05 mmol) and imidazole (6.7 mg, 0.1 mmol) were added to α-Guaiene 91% (1 g, 4.5 mmol) in a 1:1 ethanol/water mixture (20 ml), under stirring. Oxygen was bubbled into the greenish turbid mixture which was stirred at 45° C. under light irradiation with a 300 W Osram Ultra Vitalux lamp until complete conversion was detected (8-16 hours). The product distribution contained Rotundone 2 (31%), ketone 5 (9%), hydroxy-Rotundone 6 (16%) and Corymbolon 7 (1%). The green-brown turbid mixture was partially evaporated under reduced pressure and the residue extracted with tert-butyl methyl ether. The combined organic layers were dried over MgSO$_4$, filtered and evaporated. The residual brown oil (1.22 g) was bulb-to-bulb distilled at 150-230° C./0.045 mbar, giving 0.63 g Rotundone 2 of 45% GC-purity (29% corr. yield) and 0.39 g of a residue.

EXAMPLE 2. PREPARATION OF ROTUNDONE 2 FROM α-GUAIENE 1 UNDER FE(III)-CATALYSIS IN THE DARK (LIGHT EXCLUSION)

Chloro(tetraphenylporphyrinato)iron(III) (34 mg, 0.05 mmol) and imidazole (6.7 mg, 0.1 mmol) were added to α-Guaiene 91% (1 g, 4.5 mmol) in a 1:1 ethanol/water mixture (20 ml) under stirring. Oxygen was bubbled into the greenish turbid mixture at 45° C. The reaction flask was wrapped with an aluminum foil to exclude light. After 8 hours GCMS indicated complete conversion to a mixture comprising Rotundone 2 (25%), Rotundol 3 (1%), Epoxy-Guaiene 4 (4%), ketone 5 (5%), and hydroxy-Rotundone 6 (20%). The green-brown turbid mixture was evaporated partially under reduced pressure and the residue extracted with tert-butyl methyl ether. The combined organic layers were dried over MgSO$_4$, filtered and evaporated. The residual brown oil (1.22 g) was bulb-to-bulb distilled at 150-230° C./0.045 mbar, giving 0.77 g Rotundone 2 of 43% GC-purity (34% corr. yield) and 0.24 g of a residue.

EXAMPLE 3. PREPARATION OF ROTUNDONE 2 FROM α-GUAIENE 1 UNDER FE(III)-CATALYSIS AND AIR

Air was bubbled into a greenish turbid mixture of chloro(tetraphenylporphyrinato)iron(III) (34 mg, 0.05 mmol), imidazole (6.7 mg, 0.1 mmol) and α-Guaiene 91% (1 g, 4.5 mmol) in a 1:1 ethanol/water mixture (20 ml) under stirring and at 45° C. After 49 hours, GCMS indicated 96% conversion to a mixture comprising Rotundone 2 (21%), epoxy-Guaiene 4 (5%), ketone 5 (4%), hydroxy-Rotundone 6 (10%), and Corymbolon 7 (1%). After evaporation of the ethanol under reduced pressure the dark mixture was extracted with tert-butyl methyl ether against water. The combined organic layers were dried over MgSO$_4$, filtered and evaporated to 1.3 g of a brownish residue, which was purified by bulb-to-bulb distillation at 150-230° C./0.025 mbar giving 0.76 g of Rotundone 2 with 41% GC-purity (32% corr. yield) and 0.28 g of a residue.

EXAMPLES 4-12. PREPARATION OF ROTUNDONE 2 FROM α-GUAIENE 1 UNDER FE(III)-CATALYSIS IN VARIOUS SOLVENTS OR MIXTURES OF SOLVENTS

Examples 4 through 12 demonstrate the allylic oxidation of 1 g α-Guaiene 1 (91%) to the ketone (Rotundone 2) in a mixture with 1% ((chloro(tetraphenylporphyrinato)iron(III))) and 2% imidazole.

General conditions included use of 20 ml solvent or mixture of solvents at 45° C. There was no intentional irradiation of, or light exclusion of the mixture, unless otherwise indicated.

TABLE 1

| Ex. | Solvent[b] | Time [h] | Oxygen-addition | product distribution [%] compound No. | | | | | | | 2 dist. corr.[a] | purity 2 dist. |
|---|---|---|---|---|---|---|---|---|---|---|---|---|
| | | | | 1 | 2 | 3 | 4 | 5 | 6 | 7 | | |
| 4 | EtOH/H$_2$O | 8 | gas inlet | | 25 | 1 | 4 | 5 | 20 | | 34% | 43% |
| 5 | EtOH/H$_2$O | 4 | balloon | | 29 | 1 | 5 | 6 | 13 | 1 | 27% | 30% |
| 6 | H$_2$O | 24 | gas inlet | | 30 | 1 | 4 | 5 | 24 | 1 | 20% | 32% |
| 7 | iPrOH/H$_2$O | 8 | gas inlet | | 28 | | | 6 | 13 | 17 | 1 | 18% | 28% |
| 8 | MeOH/H$_2$O | 12 | gas inlet | | 29 | 1 | 4 | 4 | 16 | | 20% | 28% |
| 9 | EtOH/H$_2$O 3:1 | 30 | balloon | | 25 | | | 16 | 13 | 6 | 1 | 22% | 25% |
| 10 | EtOH/H$_2$O 1:3 | 23 | balloon | | 27 | | | 4 | 4 | 18 | | 20% | 27% |
| 11 | EtOH | 30 | balloon | 2 | 23 | | | 20 | 5 | 4 | | 18% | 21% |
| 12 | MeCN/H$_2$O 3:1 | 7 | balloon | | 24 | | | 16 | 13 | 8 | | 20% | 27% |

[a]Molar yield (in mol %) after distillation (corrected by purity of product after distillation and substrate purity).
[b]solvent mixtures are 1:1 if not otherwise indicated.

Compounds: α-Guaiene 1, Rotundone 2, Rotundol 3, epoxy-Guaiene 4, ketone 5, hydroxy-Rotundone 6, and Corymbolon 7.

Bubbling molecular oxygen through the mixture appears advantageous over introduction of the molecular oxygen via balloon.

EXAMPLES 13-15. PREPARATION OF ROTUNDONE 2 FROM α-GUAIENE 1 UNDER FE(III)-CATALYSIS WITH VARIOUS LIGANDS

Examples 13 through 15 demonstrate the allylic oxidation of α-Guaiene 1 to the ketone (Rotundone 2) with iron porphyrin catalysts having different substituted porphyrin ligands. General conditions included mixing 1 g α-Guaiene 1 (91%), 1 mol % iron porphyrin catalyst, 2 mol % imidazole, with molecular oxygen being introduced through an inlet into 20 ml of a EtOH/H$_2$O solvent mixture at a molar ratio of 1:1, at 45° C. Percentages of compounds 1-7 were determined by GCMS after isolation.

TABLE 2

| Ex. | Fe-porphyrin catalyst | time [h] | Product distribution [%] Compound No. | | | | | | | 2 dist. corr.[b] | purity 2 dist. |
|---|---|---|---|---|---|---|---|---|---|---|---|
| | | | 1 | 2 | 3 | 4 | 5 | 6 | 7 | | |
| 13 | Fe-porphyrin[a] | 8 | | 25 | 1 | 4 | 5 | 20 | | 34% | 43% |
| 14 | Fe-(pentafluorophenyl) porphyrin (CAS 36965-71-6) | 26 | | 30 | | 10 | 2 | 13 | | 27% | 31% |
| 15 | Fe-(p-methoxyphenyl) porphyrin (CAS 36995-20-7) | 31 | 1 | 29 | 1 | 3 | 5 | 19 | 1 | 10% | 13% |

[a]Fe-porph (chloro(tetraphenylporphyrinato)iron(III)).
[b]Molar yield (in mol %) after distillation (corrected by purity of product after distillation and substrate purity)

EXAMPLES 16-19. PREPARATION OF ROTUNDONE 2 FROM α-GUAIENE 1 UNDER FE(III)-CATALYSIS AT VARIOUS TEMPERATURES

Examples 16 through 19 demonstrate the allylic oxidation of 1 g α-Guaiene 1 (91%) to the ketone (Rotundone 2) in a mixture with 1% Fe-porphyrin and 2% Imidazole at various temperature conditions. General conditions included bubbling O$_2$ through an inlet for 30 minutes, then providing an O$_2$ atmosphere with a balloon, with 1000 rpm mixing of the mixture in 20 ml solvent EtOH/H$_2$O (1:1). Percentages of compounds 1-7 were determined by GCMS.

TABLE 3

| Ex. | T °C. | time [h] | 1 | 2 | 3 | 4 | 5 | 6 | 7 | 2 dist. corr.[a] | purity 2 dist. |
|---|---|---|---|---|---|---|---|---|---|---|---|
| 16 | 0-25 °C. | 24 | | 32 | | 2 | 3 | 13 | | 28% | 30% |
| 17 | 25° C. | 7 | | 32 | 1 | 3 | 4 | 13 | 1 | 24% | 27% |
| 18 | 45° C. | 8 | | 25 | 1 | 4 | 5 | 20 | | 34% | 43% |
| 19 | 80° C. | 23.5 | | 31 | | 2 | 12 | 21 | 1 | 22% | 41% |

[a]Molar yield (in mol %) after distillation (corrected by purity of product after distillation and substrate purity)

EXAMPLE 20: PREPARATION OF ROTUNDONE 2 FROM α-GUAIENE 1 AT LARGER SCALE

Oxygen was bubbled into a greenish turbid mixture of chloro(tetraphenylporphyrinato)-iron(III) (172 mg, 0.245 mmol), imidazole (67 mg, 1 mmol) and α-Guaiene 91% (10 g, 45 mmol) in a 1:1 ethanol/water mixture (200 ml) under stirring and at 45° C. After 1 h the oxygen inlet was replaced by an oxygen balloon. After another 7 h stirring at 45° C. GCMS indicated a quantitative conversion to a mixture comprising Rotundone 2 (30%), epoxy-Guaiene 4 (3%), ketone 5 (7%), hydroxy-Rotundone 6 (13%), and Corymbolon 7 (1%). After evaporation of the ethanol under reduced pressure the dark brown mixture was extracted with tert-butyl methyl ether against water. The combined organic layers were dried over MgSO$_4$, filtered and evaporated giving 14.3 g of a brownish residue, which was purified by bulb-to-bulb distillation at 150-230° C./0.1 mbar giving 8.6 g of Rotundone 2 with 38% GC-purity (33% corr. yield) and 2.3 g of a brown residue.

The invention claimed is:

1. An allylic oxidation process comprising:
   forming a mixture containing a-Guaiene and an iron (III)-X porphyrin complex catalyst, wherein X is selected from the group consisting of Cl, Br, I, mesylates, triflates, and carboxylates, in a sustainable solvent,
   introducing molecular oxygen into the mixture, and
   effecting allylic oxidation to produce an α,β-unsaturated ketone, Rotundone.

2. The process according to claim 1, wherein the mixture additionally contains a base coordination compound.

3. The process according to claim 1, including exposing the mixture to electromagnetic radiation.

4. The process according to claim 1, wherein the sustainable solvent is selected from the group consisting of water, acetone, ethanol, 2-propanol, ethyl acetate, isopropyl acetate, methanol, methyl ethyl ketone, 1-butanol, t-butanol and mixtures thereof.

5. The process according to claim 1, wherein the sustainable solvent is selected from the group consisting of cyclohexane, heptane, toluene, methylcyclohexane, methyl t-butyl ether, isooctane, acetonitrile, xylenes, dimethyl sulfoxide, acetic acid, ethylene glycol and mixtures thereof.

6. The process according to claim 1, wherein the catalyst is an iron (III) porphyrin complex catalyst, having a chloride counter-ion.

7. The process according to claim 1, wherein the porphyrin complex is a tetraphenylporphyrin complex.

8. The process according to claim 1, wherein the catalyst is selected from chloro(tetraphenylporphyrinato)iron(III) and hemin chloride.

9. The process according to claim 2, including exposing the mixture to electromagnetic radiation.

10. The process according to claim 4, wherein the sustainable solvent is selected from the group consisting of cyclohexane, heptane, toluene, methylcyclohexane, methyl t-butyl ether, isooctane, acetonitrile, xylenes, dimethyl sulfoxide, acetic acid, ethylene glycol and mixtures thereof.

11. The process according to claim 2, wherein the catalyst is an iron (III) porphyrin complex catalyst, having a chloride counter-ion.

12. The process according to claim 3, wherein the catalyst is an iron (III) porphyrin complex catalyst, having a chloride counter-ion.

13. The process according to claim 4, wherein the catalyst is an iron (III) porphyrin complex catalyst, having a chloride counter-ion.

14. The process according to claim 5, wherein the catalyst is an iron (III) porphyrin complex catalyst, having a chloride counter-ion.

15. The process according to claim 11, wherein the porphyrin complex is a tetraphenylporphyrin complex.

16. The process according to claim 12, wherein the porphyrin complex is a tetraphenylporphyrin complex.

17. The process according to claim 13, wherein the porphyrin complex is a tetraphenylporphyrin complex.

18. The process according to claim 14, wherein the porphyrin complex is a tetraphenylporphyrin complex.

19. The process according to claim 2, wherein the catalyst is selected from chloro(tetraphenylporphyrinato)iron(III) and hem in chloride.

20. The process according to claim 3, wherein the catalyst is selected from chloro(tetraphenylporphyrinato)iron(III) and hem in chloride.

21. The process according to claim 4, wherein the catalyst is selected from chloro(tetraphenylporphyrinato)iron(III) and hem in chloride.

22. The process according to claim 5, wherein the catalyst is selected from chloro(tetraphenylporphyrinato)iron(III) and hem in chloride.

23. The process according to claim 6, wherein the catalyst is selected from chloro(tetraphenylporphyrinato)iron(III) and hem in chloride.

* * * * *

UNITED STATES PATENT AND TRADEMARK OFFICE
CERTIFICATE OF CORRECTION

PATENT NO. : 10,865,173 B2
APPLICATION NO. : 16/765235
DATED : December 15, 2020
INVENTOR(S) : Fridtjof Schröder et al.

It is certified that error appears in the above-identified patent and that said Letters Patent is hereby corrected as shown below:

In the Claims

In Column 10, Claims 19-23, the word "hemin" is misspelled as "hem in".

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*